United States Patent
Lee et al.

(10) Patent No.: US 6,893,739 B2
(45) Date of Patent: May 17, 2005

(54) STEEL PLATE AND A HOT DIP GALVANIZING STEEL PLATE HAVING SUPERIOR ELECTRIC AND MAGNETIC SHIELDING PROPERTY

(75) Inventors: Jae-Young Lee, Pohang-si (KR); Eel-Young Kim, Pohang-si (KR); Jin-Gun Sohn, Pohang-si (KR); Noi-Ha Cho, Pohang-si (KR); Young-Jin Kwak, Pohang-si (KR); Soon-Joo Kwon, Pohang-si (KR); Yong-Min Kim, Pohang-si (KR); Jung-Sik Lee, Pohang-si (KR)

(73) Assignees: Posco (KR); Research Institute of Industrial Science & Technology (KR)

( * ) Notice: Subject to any disclaimer, the term of this patent is extended or adjusted under 35 U.S.C. 154(b) by 0 days.

(21) Appl. No.: 10/204,065

(22) PCT Filed: Dec. 19, 2001

(86) PCT No.: PCT/KR01/02212

§ 371 (c)(1),
(2), (4) Date: Aug. 16, 2002

(87) PCT Pub. No.: WO02/50322

PCT Pub. Date: Jun. 27, 2002

(65) Prior Publication Data

US 2003/0068521 A1 Apr. 10, 2003

(30) Foreign Application Priority Data

Dec. 19, 2000 (KR) .......................................... 2000-78772
Dec. 23, 2000 (KR) .......................................... 2000-81056

(51) Int. Cl.$^7$ ................................................ B32B 15/04
(52) U.S. Cl. ....................... 428/659; 428/626; 428/629; 428/632; 428/684; 428/685; 428/935; 148/320
(58) Field of Search .................................. 428/659, 684, 428/685, 626, 629, 632, 935; 148/320

(56) References Cited

U.S. PATENT DOCUMENTS

| | | | |
|---|---|---|---|
| 5,019,191 A | | 5/1991 | Ogata et al. |
| 5,094,920 A | * | 3/1992 | Shiozaki et al. |
| 5,411,605 A | | 5/1995 | Omori et al. |
| 5,730,810 A | * | 3/1998 | Takashima et al. |
| 5,821,686 A | * | 10/1998 | Nomura et al. |
| 6,025,673 A | | 2/2000 | Ikeda et al. |
| 6,129,992 A | * | 10/2000 | Sakuma et al. |
| 6,212,928 B1 | * | 4/2001 | Kim et al. |
| 6,282,848 B1 | | 9/2001 | Schlapfer |

FOREIGN PATENT DOCUMENTS

| | | |
|---|---|---|
| EP | 0 385 403 A1 | 9/1990 |
| EP | 0 508 479 A2 | 10/1992 |
| EP | 0 672 758 A1 | 9/1995 |
| EP | 0 852 265 A1 | 7/1998 |
| EP | 1 114 880 A | 5/1999 |
| EP | 1 098 010 A | 5/2001 |
| EP | 1 126 041 A1 | 8/2001 |
| JP | 62-185828 A | 8/1987 |
| JP | 02-145723 A | 6/1990 |
| JP | 07-032136 A | 2/1995 |
| JP | 08-98897 A | 4/1996 |
| JP | 10-096067 A | 4/1998 |
| JP | 10-208670 A | 8/1998 |
| JP | 2001-107201 A | 4/2001 |
| JP | 2001-107202 A | 4/2001 |
| JP | 2001-217589 A | 8/2001 |
| KR | 1996-005600 B1 | 4/1996 |
| KR | 1999-192767 B1 | 1/1999 |
| KR | 2001-47688 A | 6/2001 |
| KR | 10-328078 B1 | 2/2002 |
| KR | 2002-51533 A | 6/2002 |
| KR | 2002-51942 A | 7/2002 |
| KR | 2002-51993 A | 7/2002 |
| WO | WO 96/10901 A1 | 4/1996 |
| WO | WO 97/11204 A1 | 7/1998 |
| WO | WO 00/34411 A1 | 6/2000 |

* cited by examiner

Primary Examiner—Jennifer McNeil
(74) Attorney, Agent, or Firm—Webb Ziesenheim Logsdon Orkin & Hanson, P.C.

(57) ABSTRACT

A steel plate and a hot-dip galvanized steel plate, superior in terms of high electromagnetic shield capacity. The steel plate is prepared from a composition comprising C, N and S in an amount of 0.150% by weight or less in total; Mn in an amount of 0.1 to 1.0% by weight; Si in an amount of 0.5% by weight or less; Al in an amount of 1.0% by weight or less; P in an amount of 0.06% by weight or less; and Fe for the remainder, and inevitable elements, and shows a yield strength of 18 kg/mm2 or higher, and an elongation of 40% or higher. The hot-dip galvanized steel plate is prepared from a composition comprising C, N and S in an amount of 0.0150 % by weight or less in total; Mn in an amount of 0.2 to 0.8% by weight; Al in an amount of 0.6% by weight or less; Si in an amount of 0.4% by weight or less; P in an amount of 0.06% by weight or less, with the proviso that the sum of Mn, Al, Si and P amounts to 0.2–1.0% by weight; and Fe for the remainder, and inevitably present elements. In addition to having high yield strength, the hot-dip galvanized steel plate is resistant to corrosion owing to the coating of a corrosion-resistant element on the surface.

10 Claims, No Drawings

STEEL PLATE AND A HOT DIP GALVANIZING STEEL PLATE HAVING SUPERIOR ELECTRIC AND MAGNETIC SHIELDING PROPERTY

BACKGROUND OF THE INVENTION

1. Field of the Invention

The present invention relates to electromagnetic shield steel plates and hot-dip galvanized steel plates for use in construction and electric and electronic appliances, like construction panels, casings for electronic appliances, panels for power transmission lines, etc. More particularly, the present invention relates to steel plates and hot-dip galvanized steel plates which show a shield effect of 26 dB (shield efficiency 95%) or higher against electromagnetic fields at 60 Hz, a yield strength of 18~25 kg/mm$^2$, and an elongation of 40% or higher.

2. Description of the Art

Many natural and human-made sources generate electromagnetic energy in the form of electromagnetic waves. These waves consist of oscillating electric and magnetic fields which interact differently with biological systems such as cells, plants, animals, or human beings. The finding of electromagnetic waves having detrimental effects on the body has led to the development of various methods and materials for shielding electromagnetic waves. Waves adversely affecting the body are collectively called harmful waves.

Recent studies have demonstrated harmful effects of electromagnetic waves at low frequencies on biological systems. Particularly, a series of studies results revealing the interrelation of the electromagnetic field (60 Hz) around power transmission lines with carcinogenesis has had great repercussions all over the world.

In addition to carcinogenic effects, low frequency waves with magnetic properties are found to cause inductive currents in the body upon exposure to the waves for a long period of time, upsetting the biological balance of various ions, such as Na+, K+, Cl− and so forth, across cellular membranes, which results in adversely affecting the hormone secretion and immunocytes of the body.

Further, other studies showed the influence of magnetic fields on the secretion of melatonin, a hormone responsible for regulating the sleep cycle, adding that the body may suffer from insomnia upon prolonged exposure to magnetic fields.

Recent legislation, in response to environmental concerns stemming from adverse health effects of electromagnetic fields, has been enacted to lower the acceptable levels of electromagnetic waves emitted from various electrical or electromagnetic appliances in many countries. Further, the regulation concerning electromagnetic waves is used as an import barrier against electric and/or electromagnetic appliances. For example, Sweden and other European countries prohibit the import of TVs or computer monitors that show a magnetic leakage of 2 mG or higher.

Likewise, in Korea, there was enacted a law which regulates exposure limits of electric and magnetic fields by frequency bands (Standards for human body protection from electromagnetic waves, Notification No. 2000-91 of the Ministry of Information and Communication of Korea). Also, there is a legislation notification by which electromagnetic waves will be treated as environmental pollution sources (Publication No. 2001-77 of the Ministry of the Environment of Korea).

In order to cope with such harmful electromagnetic waves, shielding technology has been developed in two aspects: structure and material. With regard to the construction aspect, magnetically shielded rooms are disclosed in U.S. Pat. No. 6,282,848 and Japanese Pat. Laid-Open Publication No. Hei. 7-32136. Electrically conductive materials such as copper are in current use as shields against electromagnetic waves, as disclosed in Japanese Pat. Laid-Open Publication No. 2001-217589. However, such materials are useful only for electromagnetic waves at high frequencies (1 KHz or higher).

Electromagnetic waves at 60 Hz, usually detected in general power sources, are composed of an electric field and a magnetic field component, which both vary with time. Accordingly, in order to shield these low frequency electromagnetic waves, which have recently been shown to have adverse health effects, time-varying electric and magnetic fields should be considered together. However, there have not yet been developed practical technologies for steel plates that can effectively shield time-varying electromagnetic fields.

Conventionally, steel plates with high magnetic permeability are used as electromagnetic shields. For instance, Japanese Pat. Laid-Open Publication Nos. Hei. 10-208670 and Hei. 10-96067 and PCT WO 97/11204 disclose static magnetic field-shielding steel plates which can be adopted in color image tubes of, for example, TV monitors, with the aim of preventing color modulation on the monitors. Such steel plates are used to take advantage of their coercive force and permeability under static magnetic field such as earth magnetic field, but cannot cope with time-varying magnetic and electric fields. Accordingly, the conventional steel plates are somewhat different from electromagnetic wave shields.

As occasion demands, construction materials are required to not permit the permeation of electromagnetic waves thereto. In this regard, hot-rolled thick plates using silicon steel are suggested for use in electromagnetic field shield constructions, as disclosed in Japanese Pat. Laid-Open Publication Nos. 2001-107201 and 2001-107202. The construction materials, however, take advantage only of the high permeability of silicon steel under static magnetic fields, and are not described in terms of shield effect of electric fields. Further, the steel plates are poor in formability and platability (the property of galvanized coating) because they are not cold-rolled but hot-rolled.

Also, the present inventors disclosed a steel material with excellent magnetic shield effect at low frequencies in Korean Pat. Appl'n No. 1999-52018. The shield capacity is a theoretical value obtained from the permeability and conductivity measured under static magnetic fields, and thus differs from real values, finding difficulty in practical application. Thus, there remained a need for shield evaluation under time-varying magnetic fields.

Meeting this need, methods for evaluating the magnetic shielding capacity of steel plates according to frequencies were developed (Korean Pat. Nos. 2000-799907 and 2000-80886), and are in current use.

Typically, the shielding efficiency of a steel plate can be obtained by the following equations:

$$\text{Magnetic Shield Efficiency} = \frac{\text{Applied Magnetic Field} - \text{Transmitted Magnetic Field}}{\text{Applied Magnetic Field}} \times 100 \quad \text{Equation 1}$$

$$\text{Electric Shield Efficiency} = \frac{\text{Applied Electric Field} - \text{Transmitted Electric Field}}{\text{Applied Electric Field}} \times 100 \quad \text{Equation 2}$$

Expressed as dB units, the shield effect of a steel plate can be obtained by the following equations:

$$\text{Magnetic Shield Effect} = -20 \log \frac{\text{Transmitted Magnetic Field}}{\text{Applied Magnetic Field}} \quad \text{Equation 3}$$

$$\text{Electric Shield Effect} = -20 \log \frac{\text{Transmitted Electric Field}}{\text{Applied Electric Field}} \quad \text{Equation 4}$$

According to the equations, the shield effect of a shielding material having a shielding efficiency of 90% (attenuation of electromagnetic waves to one tenth) can be expressed as 20 dB. A shielding efficiency of 95% (attenuation of electromagnetic waves to one twentieth) corresponds to a shield effect of about 26 dB.

Korean Pat. Appl'n No. 2000-81056 to the present inventors is directed to a biowave steel plate based on an electromagnetic shielding cold-rolled steel plate on which powders emitting far-infrared radiation are coated. To improve the shield effect against time-varying magnetic fields, that is, to obtain high permeability under time-varying magnetic fields, the biowave steel plate for shielding electromagnetic waves contains carbon in an amount of 0.02% or less and Si in an amount of 0.5–3.5%.

Superior as it is in electromagnetic shield effect, the cold-rolled steel plate with a carbon content of 0.02% or less is found to be poor in strength not only because its steel structure becomes coarse in terms of grain size, but also because it has low strain due to reduction of carbon solid solution and it has less carbon precipitate. Therefore, the steel plate is not suitable for use in construction and furniture that require appropriate strength.

Silicon steel plates with a silicon content of 0.5–3.5% show excellent magnetic shield effect, but shield electric fields only poorly. Particularly, such silicon steel plates are too high in strength and very poor in formability (elongation 40% or less), so that they are very difficult to apply to construction and household appliances which require formability of materials. In the case that silicon steel plates are laminated for use in magnetic cores, an electric insulating material is coated on the surface of the laminate structure to minimize eddy current loss. Thus, it is impossible to plate the silicon steel with corrosion resistant materials such as zinc. Additionally, the silicon steel plates are expensive because they are not produced by the general cold rolled process (at an annealing temperature of 900° C. or less), but annealed at high temperatures (higher than 900° C.) in special furnaces. For these reasons, silicon steel plates are not suitable as panel materials for construction and household electronic appliances.

For use in exterior environments, like construction exterior finishes, silicon steel plates must be corrosion-resistant. In this regard, hot-dip galvanizing with anti-corrosive materials is carried out on such exterior finishes. According to the present inventors' experiment in which silicon steel plates are coated with zinc by hot-dip galvanizing after being deprived of electric insulating materials, it was found that the silicon steel plates are poorly coated owing to the presence of Si.

SUMMARY OF THE INVENTION

Leading to the present invention, the thorough and intensive research to electromagnetic shield steel plates suitable for use in construction and electronic appliance, resulted in the finding that interstitial elements C, N, and S as well as additive elements Si, Al, Mn and P have great influence on the electromagnetic shield effect and strength of the steel plate and that contents of the additive elements are related to the hot-dip galvanization of the steel plate.

Therefore, it is an object of the present invention to overcome the above problems encountered in prior arts and to provide a steel plate and a hot-dip galvanized steel plate which shows a shield effect of 26 dB (shield efficiency 95%) or higher against time-varying electromagnetic fields at 60 Hz on the basis of 1 mm thickness of the plate, a yield strength of 18~25 kg/mm$^2$, and an elongation of 40% or higher.

In accordance with an aspect of the present invention, there is provided a steel plate with electromagnetic shield effect, prepared from a composition comprising C, N and S in an amount of 0.0150% by weight or less in total; Mn in an amount of 0.1 to 1.0% by weight; Si in an amount of 0.5% by weight or less; Al in an amount of 1.0% by weight or less; P in an amount of 0.06% by weight or less; and Fe for the remainder, and inevitably present elements.

In accordance with another aspect of the present invention, there is provided a hot-dip galvanized steel plate with high electromagnetic shield capacity and yield strength, prepared from a composition comprising C, N and S in an amount of 0.0150% by weight or less in total; Mn in an amount of 0.2 to 0.8% by weight; Al in an amount of 0.6% by weight or less; Si in an amount of 0.4% by weight or less; P in an amount of 0.06% by weight or less, with the proviso that the sum of Mn, Al, Si and P amounts to 0.2~1.0% by weight; and Fe for the remainder, and inevitably present elements.

DETAILED DESCRIPTION OF THE INVENTION

The present invention pertains to steel plate shields against electric and magnetic fields. Magnetic fields are generated by currents, while electric fields are induced by voltages. At low frequencies, electromagnetic waves are separated into electric and magnetic components. To be used as an electromagnetic shield, a material must attenuate or shield both of the electric and magnetic components.

The magnetic shield effect of a material against magnetic fields at low frequencies is determined by the ability to alter magnetic flux paths and to cause eddy current loss. Herein, the alteration of a magnetic flux path means that, when a harmful magnetic field is incident upon a shield material, a path through which the magnetic field can flow is generated on the surface of the material, so that the magnetic field is not led to an interior of the shield material, but guided elsewhere to dissipate. Herein, the eddy current loss indicates that, when being incident upon a shield material, a magnetic field in wave form is dissipated as heat energy at the surface of the shield material by an eddy current which circulates on the material in the direction of eliminating the magnetic field. Materials with higher permeability are more advantageous in the alteration of magnetic flux paths. Also, the eddy current loss generated at low frequencies is typically increased with increasing of the electric conductivity and permeability of a shield material. Hence, steel plates with high permeability and electric conductivity at 60 Hz exhibit excellent low-frequency magnetic field shielding properties.

Electric fields can be induced upon generation of potential differences even if currents do not flow. To prevent the induction of an electric field in a shielded space, it must be in an equipotential state. Desirable as electric shields are materials with high volume electric conductivity because higher electric conductivity is more advantageous in preventing the generation of a potential difference.

In the experience of the present inventors, it was very difficult to exactly measure the electric conductivity and magnetic permeability of a material in the presence of a time-varying electric field, such as electromagnetic waves. In addition, the preparation of samples was so complex as to cause large error in the measurement of the conductivity and permeability.

In the present invention, steel plates are measured for shield effect against magnetic and electric fields. In this regard, low-frequency magnetic shield effect was evaluated by use of an apparatus for measuring magnetic shield effect under time-varying magnetic fields (Korean Pat. Nos. 2000-79907 and 2000-80886). As for shield effect against time-varying electric fields, it is determined by the ratio of electric field intensities measured in a shielded space in the presence of and in the absence of a shielding material using a voltage source of 1,200 volts/m at 60 Hz, positioned outside of the shielded room.

Steel plates may comprise various elements in addition to Fe. The alloy elements that are generally added to ferromagnetic Fe to improve the strength and corrosive resistance of steel plates, affect the maximal permeability and electric conductivity of steel plate under time-varying magnetic fields (60 Hz). Also, the permeability and electric conductivity varies with the carbon content and grain size of the steel plate. Of course, steel plates show different mechanical properties according to composition due to the change of strengthening mechanisms such as solid-solution hardening, grain size refinement, etc.

In accordance with the present invention, there is provided a steel plate which has a strength suitable for use in construction and furniture panels, that is, a yield strength of 18–25 kg/mm$^2$, as well as an electromagnetic shield capacity of 95% (26 dB) or higher. Through the thorough and intensive experiments conducted by the present inventors, in which steel plates were measured for electromagnetic shield effect and mechanical strength while being changed in composition, the role of each component in determining the electromagnetic shield effect and strength of the steel plate are defined. Particularly, C, N, S, Si, Al, Mn and P were found to have great influence on the electromagnetic shield effect and mechanical strength of the steel plate. Based on the results of the experiments, an optimal steel composition system could be obtained.

Additional experiments resulted in the finding that contents of additive elements, such as Si, Al and Mn, are related to the hot-dip galvanization of the steel plate, leading to a steel composition superior in hot-dip platability as well as shield effect and strength.

On the whole, the electromagnetic shield effect of a steel plate is largely dependent on its content of interstitial elements such as N, C and S, or elements which can form the precipitate. For instance, the internal strain of steel increases with increasing of the content of C, N and S and increase the strength due to strain-hardening. Also, the interstitial elements C, N and S are precipitated as forms of Fe3C, AlN and MnS, respectively, thereby increasing the strength of the steel.

However, the increased strain and formed deposits give rise to a great decrease in the permeability and electric conductivity of the steel, thus deteriorating shield properties of the steel. In fact, it is very difficult to provide steel with an appropriate strength as well as a shield efficiency of 95% or higher by use of such interstitial elements only.

In accordance with the present invention, the sum of C, N and S, which have a fatal influence on electromagnetic shield properties of steel plates, is limited to up to 0.015% by weight in the composition of the steel.

Preferably, C and N are each contained in an amount of 0.0030% or less, while the content of S is controlled in an amount of 0.0090%, so as to ensure the steel being of electromagnetic shield capacity and mechanical formability.

Where the interstitial elements C, N and S are used in the above-defined amounts, the steel becomes poor in strength. In order to compensate for the weak strength attributed to the minimal contents of the interstitial elements, other elements are needed to induce such solid-solution hardening as to increase the strength of the steel. However, restrictions must be imposed on the amount and kind of elements used to improve strength, lest they deteriorate the electromagnetic shield effect by inducing too large a decrease in permeability and electric conductivity.

Si is contained in the steel plate of the present invention. Increasing the content of Si may increase the strength of the steel, but may decrease the magnetic shield capacity. Particularly, the steel plate containing more than 0.5% by weight of Si is greatly decreased in elongation, as well as becoming significantly poor in magnetic shield capacity, so that it is unsuitable as a magnetic field shielding panel for use in construction and household electric appliances that must have sufficient mechanical formability. In accordance with the present invention, therefore, the content of Si is limited to up to 0.5% by weight. Commonly, silicon steel plates with higher Si contents have higher permeability and thus are of better magnetic shield effect. However, these effects cannot be enjoyed in the present invention because the steel plate of the present invention is manufactured according to a typical cold roll process without undergoing a hot annealing process characteristically conducted for common silicon steel plates.

Al is also contained in the steel plate of the present invention. Al improves the strength of the steel without a significant reduction in shield effect against magnetic and electric fields. Up to 1.0% by weight of Al is contained in the steel plate of the present invention. More than 1.0% by weight of Al gives rise to a great decrease in shield capacity against magnetic and electric fields and limits the elongation of the steel plate to less than 40%.

In electromagnetic shield effect and mechanical properties, Al shows behaviors similar to those of Si. It is believed that the similar behaviors are attributed to the similarity between the two elements in terms of their influence on the permeability and conductivity of the steel plate as well as in strengthening mechanism.

The steel plate of the present invention also comprises Mn. There is no change in the electric shield capacity of the steel plate even when much Mn is contained, because the element does not affect the electric conductivity of the steel plate. However, the mechanical properties and magnetic shield effect of the steel plate vary greatly with Mn content.

To an amount of 0.1% by weight, Mn generally makes contribution to the magnetic shield effect (26 dB or higher) and elongation (40% or higher) of the steel plate, in addition to guaranteeing an appropriate strength (yield strength 18 kg/mm$^2$). However, the magnetic shield effect is not further improved when more than 1.0% by weight of Mn is added.

As for the elongation, it is decreased, rather, in the presence of more than 1.0% by weight of Mn. Considering these effects, Mn is used in an amount of 0.1 to 1.0% by weight.

While acting to strengthen the steel, P does not significantly affect electric and magnetic shield effect at an amount less than 0.06% by weight. When containing more than 0.06% by weight of P, the steel plate is abnormally increased in strength to 25 kg/mm$^2$ or higher while becoming poor in shield effect. Accordingly, the amount of P in the steel plate of the present invention is limited to less than 0.06% by weight.

Except for elements inevitably present during the manufacture of the steel plate, other elements such as Ti, V and Nb are preferably excluded from the steel plate of the present invention because they make the grain size fine in addition to greatly deteriorating low-frequency magnetic field shield properties. Thus, the steel plate of the present invention is preferably exclusive of as many elements as possible that cause the reduction of grain sizes.

In order to provide corrosion resistance to the steel plate comprising the above-defined composition, it may be electroplated. For instance, a steel plate coated with a zinc layer can exhibit the same electromagnetic shield effect as a bare steel plate. The reason is that the zinc coating is very thin and has almost no magnetic properties.

To improve the corrosive resistance of the cold-rolled steel plate of the composition, the steel plate may be hot-dip galvanized with zinc or aluminum.

Since Si, Al and Mn have great influence on the hot-dip galvanization of the steel plate, plating defects may occur if the steel plate itself is subjected to hot-dip galvanizing. Therefore, in accordance with the present invention, there is provided a hot-dip galvanized steel plate whose elements are so optimally controlled as to prevent the occurrence of plating defects.

To guarantee the hot-dip galvanization of the steel plate, Si is preferably contained in an amount of 0.4% by weight or less. If present in too large an amount, Si, which is readily oxidized, forms $SiO_2$ on the surface of the cold-rolled steel plate and the oxide adversely affects the coatability. Within the Si range of 0.2–0.4% by weight, the steel plate has a somewhat dark surface, which differs from plating defects, after being hot-dip galvanized. This problem can be solved through a subsequent skin pass process. Herein, skin pass means rolling under a very low load, which is conducted in the final stage of product production in order to control the shape and roughness of steel plate. Therefore, it is more preferred to limit the Si content to 0.2% by weight or less so as to not conduct such an additional skin pass process after hot-dip galvanizing.

In terms of the hot-dip galvanization of the steel plate, it is preferable that the steel plate contains Al in an amount of 0.6% by weight or less. An Al content exceeding 0.6% by weight degrades the coatability of the steel plate, thereby causing plating defects. Slight hot-dip galvanizing defects may be observed in the steel plate containing 0.4–0.6% by weight of Al, but can be removed by a skin pass process subsequent to the hot-dip galvanizing process. Therefore, omission of such an additional subsequent skin pass process, which is preferable, requires the limitation of the Al content to 0.4% by weight or less.

As for the Mn content, it is preferably defined in the range of 0.2 to 0.8% by weight. For instance, when too little Mn is used, it is difficult to guarantee the strength of the steel plate will reach an appropriate level. On the other hand, more than 0.8% by weight of Mn is apt to cause defects upon hot-dip galvanizing.

In accordance with the present invention, the sum of Mn, Si, Al and P falls within the range of 0.2 to 1.0% by weight of the steel plate. When the sum of Mn, Si, Al and P is below 0.2% by weight, the strength of the steel plate can be increased to only up to 18 kg/mm$^2$. The steel plate containing Mn, Si, Al and P all together in an amount more than 1% by weight has significantly poor magnetic shield effect and suffers from the occurrence of hot-dip galvanizing defects.

In an aspect of the hot-dip galvanizing properties, contents of the other component elements P, C, N and S are also as defined above.

By controlling the contents of the additive elements, as described above, hot-dip galvanized steel plates with superior electromagnetic shield effect and hot dip galvanizing properties can be effectively manufactured.

In accordance with the present invention, the steel plate may be coated with an organic resin layer so as to express a color on the steel plate. After being coated with a pigment-containing organic resin such as polyethylene or acryl, the steel plate, so-called PCM (pre-coated metal) steel plate, maintains the characteristic electromagnetic shield capacity and mechanical properties that it has before, not only because the pigment contained in the resin is non-magnetic but also because the thickness of coating is as thin as 25 μm.

In accordance with the present invention, far-infrared radiation a radiation efficiency, so called emissivity, of 0.9, or higher may be formed to a thickness of 15 to 60 μm on the electrically plated or hot-dip galvanized coating layer of the steel plate. Preferably, the far-infrared radiation emitting powder has a specific surface area of 1 m2/g or higher and comprises 17–99% of $Mg(OH)_2$.

Having generally described this invention, a further understanding can be obtained by reference to certain specific examples which are provided herein for purposes of illustration only and are not intended to be limiting unless otherwise specified.

EXAMPLE 1

To examine the effects of the interstitial elements N, C and S on electromagnetic shield capacity, steel slabs with different compositions were prepared with different N, C and S contents as shown in Table 1, below, and 30 kg of each steel composition was melted under vacuum. In Table 1, the expression "Tr" means no addition of the element.

The steel slabs were re-heated at 1,250° C., and hot-rolled with the temperature terminating at 900° C., to give hot-rolled steel plates each 2 mm thick. Hot-rolled scales were removed from the steel plates by pickling with acid. The acid-pickled hot-rolled steel plates were cold-rolled to a thickness of 1 mm at a reduction percentage of 50%. Subsequently, using a consecutive annealing simulator, annealing was carried out at 850° C. to produce cold-rolled steel plates.

With the aid of an electromagnetic shield effect analyzer, each of the cold-rolled steel plates was measured for electromagnetic shield effect at 60 Hz, and the results are given in Table 1, below. Also, the mechanical properties, such as yield strength and elongation, of the steel plates, were measured by use of a universal testing machine and summarized in Table 1, below.

TABLE 1

| Composition No. | Component (Wt %) | | | | | | Magnetic Shield (dB) | Electric Shield (dB) | Yield Strength (Kg/mm$^2$) | Elong. (%) |
|---|---|---|---|---|---|---|---|---|---|---|
| | C | N | S | Si | Al | Mn | | | | |
| C. 1 | 0.0025 | 0.0015 | 0.0080 | Tr. | Tr. | Tr. | 28.3 | 41.4 | 14.8 | 51 |
| C. 2 | 0.0100 | 0.0030 | 0.0080 | Tr. | Tr. | Tr. | 16.2 | 40.4 | 22.1 | 43 |
| C. 3 | 0.0025 | 0.0080 | 0.0080 | Tr. | Tr. | Tr. | 21.3 | 41.0 | 20.8 | 42 |
| 1 | 0.0020 | 0.0020 | 0.0080 | 0.2 | Tr. | 0.2 | 27.9 | 40.1 | 22.3 | 43 |
| 2 | 0.0025 | 0.0025 | 0.0090 | 0.1 | Tr. | 0.1 | 27.7 | 40.1 | 18.7 | 46 |
| C. 4 | 0.0020 | 0.0020 | 0.0160 | 0.2 | Tr. | 0.2 | 23.9 | 40.1 | 25.1 | 39 |
| C. 5 | 0.0030 | 0.0080 | 0.0100 | 0.2 | Tr. | 0.2 | 22.2 | 39.9 | 25.3 | 38 |
| C. 6 | 0.0100 | 0.0025 | 0.0080 | 0.2 | Tr. | 0.2 | 15.4 | 39.8 | 27.2 | 36 |

As apparent from the data of Table 1, the steel plates of the present invention (Composition Nos. 1 and 2), each of which maintained C, N and S below 0.0150% by weight in total and contained appropriate amounts of Si and Mn respectively, showed excellent electric and magnetic shield effects, both found to be more than 26 dB (shield efficient 95%), and had yield strengths higher than 18 kg/mm$^2$. Their mechanical formability was also found to be excellent in terms of elongation (higher than 40%).

In contrast, Comparative Composition No. C. 1, which was low in contents of N, C and S, was superior to both electric and magnetic shield effects, but its strength was too low to be suitable for use in the present invention.

Superior as they were in strength, Comparative Composition Nos. C. 2 to C. 6 whose N, C and S contents exceeded the upper limit of the range defined in the present invention were found to be very poor in magnetic shield effect with a significant reduction in electric shield effect.

EXAMPLE 2

An examination was made of the influence of Si and Al on the electromagnetic shield effect and mechanical properties of steel plates. In this regard, steel slabs with different compositions were prepared with different Si and Al contents as shown in Table 2, below, and 30 kg of each steel composition was vacuum melted. In Table 2, the expression "Tr" means no addition of the element.

After being re-heated at 1,250° C., the steel slabs were hot-rolled with the temperature terminating at 900° C., to give hot-rolled steel plates each 2 mm thick. The steel plates were pickled with acid to remove hot-rolled scales therefrom. The acid-pickled hot-rolled steel plates were cold-rolled to a thickness of 1 mm at a reduction percentage of 50%. Subsequently, using a consecutive annealing simulator, annealing was carried out at 850° C. to produce cold-rolled steel plates.

With the aid of an electromagnetic shield effect analyzer, each of the cold-rolled steel plates was measured for electromagnetic shield effect at 60 Hz, and the results are given in Table 2, below. Also, the mechanical properties, such as yield strength and elongation, of the steel plates, were measured by use of a universal testing machine and summarized in Table 2, below.

TABLE 2

| Composition No. | Component (wt %) | | | | | | Magnetic Shield (dB) | Electric Shield (dB) | Yield Strength (Kg/mm$^2$) | Elong. (%) |
|---|---|---|---|---|---|---|---|---|---|---|
| | C | N | Si | Al | Mn | P | | | | |
| 3 | <0.003 | <0.003 | 0.2 | Tr. | 0.2 | Tr. | 27.9 | 40.1 | 22.3 | 43 |
| 4 | <0.003 | <0.003 | 0.4 | Tr. | 0.2 | Tr. | 26.8 | 38.4 | 24.8 | 41 |
| C. 7 | <0.003 | <0.003 | 0.6 | Tr. | 0.2 | Tr. | 25.5 | 37.9 | 27.5 | 39 |
| C. 8 | <0.003 | <0.003 | 0.8 | Tr. | 0.2 | Tr. | 22.7 | 37.9 | 29.2 | 36 |
| 5 | <0.003 | <0.003 | Tr. | 0.4 | 0.2 | Tr. | 26.6 | 39.8 | 21.4 | 45 |
| 6 | <0.003 | <0.003 | Tr. | 0.8 | 0.2 | Tr. | 26.1 | 38.6 | 21.2 | 43 |
| C. 9 | <0.003 | <0.003 | Tr. | 1.2 | 0.2 | Tr. | 25.4 | 37.5 | 24.5 | 38 |
| C. 10 | <0.003 | <0.003 | Tr. | 1.6 | 0.2 | Tr. | 24.1 | 36.7 | 26.2 | 36 |

As seen in Table 2, steel plates of Composition Nos. 3 to 6, which contained the sum of C, N and S in the range of the present invention and appropriate amounts of Si and Al, showed excellent electric and magnetic shield effects, both found to be more than 26 dB (shield efficient 95%), and had yield strengths higher than 18 kg/mm$^2$. Their formability was also found to be excellent in terms of elongation (higher than 40%).

In contrast, Comparative Composition Nos. C. 7 and C. 8 whose Si contents were over 0.5% were greatly decreased in elongation as well as in magnetic shield effect. Thus, they are not suitable as a magnetic field shielding panel for use in construction and household electric appliances.

Comparative Composition Nos. C. 9 and C. 10 whose Al contents were over 1.0%, although improved in strength, were low in both electric and magnetic shield effects, in addition to showing elongations lower than 40%. Thus, they are also unsuitable for use in the present invention.

EXAMPLE 3

Steel slabs with different compositions were prepared with different Mn and P contents as shown in Table 3, below, and 30 kg of each steel composition was vacuum melted. In Table 3, the expression "Tr" means no addition of the element.

After being re-heated at 1,250° C., the steel slabs were hot-rolled with the temperature terminating at 900° C., to give hot-rolled steel plates each 2 mm thick. The steel plates were removed of hot-rolled scales by pickling acid, followed by cold-rolling the acid-pickled hot-rolled steel plates to a thickness of 1 mm at a reduction percentage of 50%. Subsequently, using a consecutive annealing simulator, annealing was carried out at 850° C. to produce cold-rolled steel plates.

With the aid of an electromagnetic shield effect analyzer, a measurement was made of electromagnetic shield effect at 60 Hz of each of the cold-rolled steel plates, and the results are given in Table 3, below. Also, the mechanical properties, such as yield strength and elongation, of the steel plates, were measured by use of a universal testing machine and summarized in Table 3, below.

TABLE 3

| Composition No. | Component (Wt %) | | | | | | Magnetic Shield (dB) | Electric Shield (dB) | Yield Strength (Kg/mm$^2$) | Elong. (%) |
|---|---|---|---|---|---|---|---|---|---|---|
| | C | N | Si | Al | Mn | P | | | | |
| 7 | <0.003 | <0.003 | 0.2 | Tr. | 0.1 | Tr. | 27.3 | 40.1 | 23.5 | 41 |
| 8 | <0.003 | <0.003 | 0.2 | Tr. | 0.3 | Tr. | 27.7 | 40.0 | 21.8 | 45 |
| 9 | <0.003 | <0.003 | 0.2 | Tr. | 0.5 | Tr. | 27.9 | 40.0 | 19.5 | 48 |
| 10 | <0.003 | <0.003 | 0.2 | Tr. | 0.7 | Tr. | 26.0 | 39.9 | 21.3 | 43 |
| C. 11 | <0.003 | <0.003 | 0.2 | Tr. | 0.9 | Tr. | 24.7 | 39.9 | 23.5 | 40 |
| 11 | <0.003 | <0.003 | Tr. | Tr. | 0.7 | Tr. | 26.6 | 40.3 | 21.4 | 45 |
| 12 | <0.003 | <0.003 | Tr. | Tr. | 0.9 | Tr. | 26.1 | 40.1 | 23.1 | 41 |
| C. 12 | <0.003 | <0.003 | Tr. | Tr. | 1.1 | Tr. | 25.4 | 40.1 | 25.2 | 38 |
| 13 | <0.003 | <0.003 | 0.3 | 0.3 | 0.2 | Tr. | 26.2 | 38.5 | 24.1 | 42 |
| 14 | <0.003 | <0.003 | 0.3 | 0.3 | 0.2 | 0.04 | 26.0 | 38.2 | 24.7 | 41 |
| C. 13 | <0.003 | <0.003 | 0.3 | 0.3 | 0.2 | 0.08 | 23.8 | 38.2 | 27.3 | 36 |

As seen in Table 3, steel plates of Composition Nos. 7 to 14, which contained the sum of C, N and S in the range of the present invention and appropriate amounts of Mn, Si and Al, showed excellent electric and magnetic shield effects, both found to be more than 26 dB (shield efficient 95%), and had yield strengths higher than 18 kg/mm$^2$. Their formabilty was also found to be excellent in terms of elongation (higher than 40%).

In contrast, Comparative Composition Nos. C. 11 and C. 12 with Mn contents exceeding 0.8% showed poor a magnetic shield effect, as well as being deteriorated in terms of elongation. Comparative Composition No. C. 13 with a P content of more than 0.06% was also unsuitable for use in applications meeting the present invention, owing to its poor elongation and shield effect.

EXAMPLE 4

On the cold-rolled steel plates manufactured in Composition Nos. 1 to 3, zinc was electroplated (electrolytically galvanized) at 65° C. at a coating density of 15 g/m2 by use of an electroplating simulator. Analysis showed that the steel plates retain the same electromagnetic shield effect and mechanical properties as before the electroplating. This was due to the fact that the zinc coating layer is not magnetic in addition to being as thin as 2.5 μm. Thus, the cold-rolled steel plates of the present invention are of excellent electromagnetic shield effect and can be made to be resistant to corrosion.

EXAMPLE 5

Steel slabs with different compositions were prepared with different Si and Al contents as shown in Table 4, below, and 30 kg of each steel composition was vacuum melted. In Table 4, the expression "Tr" means no addition of the element.

After being re-heated at 1,250° C., the steel slabs were hot-rolled with the temperature terminating at 900° C., to give hot-rolled steel plates each 2 mm thick. The steel plates were pickled with acid to remove hot-rolled scales therefrom. Then, the acid-pickled hot-rolled steel plates were cold-rolled to a thickness of 1 mm at a reduction percentage of 50%. Subsequently, using a consecutive annealing simulator, annealing was carried out at 850° C. to produce cold-rolled steel plates which were then hot-dip galvanized with zinc to a coating density of 300 g/m2 by use of a hot-dip galvanizing simulator.

With the aid of an electromagnetic shield analyzer, each of the galvanized, cold-rolled steel plates was measured for electromagnetic shield effect at 60 Hz, and the results are given in Table 4, below. Also, the mechanical properties, such as yield strength and elongation, of the steel plates, were measured by use of a universal testing machine and summarized in Table 4, below.

Determined through observation with the naked eye and testing for coat adhesion, the platability of the hot-dip galvanized steel plates was expressed as ○ for a good state, Δ for the presence of curable plating defects which can be removed by subsequent skin pass process, and as X for the presence of incurable and fatal plating defects, in Table 4.

TABLE 4

| Composition No. | Component (Wt %) | | | | | | Magnetic Shield (dB) | Electric Shield (dB) | Yield Strength (Kg/mm$^2$) | Hot-Dip Platability |
|---|---|---|---|---|---|---|---|---|---|---|
| | C | N | Si | Al | Mn | P | | | | |
| 1 | <0.003 | <0.003 | 0.2 | Tr. | 0.2 | Tr. | 28.1 | 40.5 | 22.0 | ○ |
| 2 | <0.003 | <0.003 | 0.4 | Tr. | 0.2 | Tr. | 26.9 | 38.9 | 24.0 | Δ |
| C. 1 | <0.003 | <0.003 | 0.6 | Tr. | 0.2 | Tr. | 25.5 | 38.2 | 27.4 | X |

TABLE 4-continued

| Composition | Component (Wt %) | | | | | | Magnetic Shield | Electric Shield | Yield Strength | Hot-Dip |
| --- | --- | --- | --- | --- | --- | --- | --- | --- | --- | --- |
| No. | C | N | Si | Al | Mn | P | (dB) | (dB) | (Kg/mm$^2$) | Platability |
| C. 2 | <0.003 | <0.003 | 0.8 | Tr. | 0.2 | Tr. | 22.8 | 38.0 | 28.6 | X |
| 3 | <0.003 | <0.003 | Tr. | 0.2 | 0.2 | Tr. | 26.9 | 40.5 | 20.6 | ○ |
| 4 | <0.003 | <0.003 | Tr. | 0.4 | 0.2 | Tr. | 26.5 | 39.9 | 21.3 | ○ |
| 5 | <0.003 | <0.003 | Tr. | 0.6 | 0.2 | Tr. | 26.1 | 39.2 | 23.3 | Δ |
| C. 3 | <0.003 | <0.003 | Tr. | 0.8 | 0.2 | Tr. | 25.4 | 38.8 | 22.5 | X |
| 6 | <0.003 | <0.003 | 0.3 | 0.3 | 0.2 | Tr. | 26.1 | 38.5 | 24.1 | ○ |
| C. 4 | <0.003 | <0.003 | 0.3 | 0.4 | 0.2 | Tr. | 24.2 | 38.2 | 25.8 | ○ |
| C. 5 | <0.003 | <0.003 | 0.3 | 0.6 | 0.2 | Tr. | 21.6 | 37.7 | 26.3 | X |

As apparent from the data of Table 4, the steel plates of the present invention (Composition Nos. 1 to 6), each of which maintained C, N and S below 0.0150% by weight in total and contained the sum of Mn, Al, Si and P in an appropriate amount, all were excellent in yield strength and electric and magnetic shield capacity in addition to showing generally good platability. Particularly as for the platability, it was found to be better when Al and Si contents were controlled below 0.4 and 0.2%, respectively (Composition Nos,1 3, 4 and 6) than otherwise (Composition Nos. 2 and 5).

On the other hand, Comparative Composition Nos. C. 1 and C. 2 with Si contents of more than 0.4% exhibited poor platability so that plating defects were observed. This was believed to be attributed to the fact that Si, readily oxidized, formed much SiO$_2$ on the surface of the steel plates.

Serious plating defects were also observed in Comparative Composition No. C. 3 in which the Al content was over 0.6%.

Where the sum of Mn, Al, Si and P exceeded 1.0% even if Mn, Si and Al were individually within the content ranges defined according to the present invention (Comparative Composition Nos. C. 4 and C. 5), the steel plates showed poor platability in terms of coating adhesion after hot-dip galvanization, with a decrease in magnetic shield effect.

EXAMPLE 6

Steel slab with different compositions were prepared with different Mn contents as shown in Table 5, below, and 30 kg of each steel composition was vacuum melted. In Table 5, the expression "Tr" means no addition of the element.

After being re-heated at 1,250° C., the steel slabs were hot-rolled with the temperature terminating at 900° C., to give hot-rolled steel plates each 2 mm thick. Hot-rolled scales were removed from the steel plates by pickling with acid. Thereafter, the acid-pickled hot-rolled steel plates were cold-rolled to a thickness of 1 mm at a reduction percentage of 50%. Subsequently, using a consecutive annealing simulator, annealing was carried out at 850° C. to produce cold-rolled steel plates which were then hot-dip galvanized with zinc to a coating density of 300 g/m2 by use of a hot-dip galvanizing simulator.

With the aid of an electromagnetic shield effect analyzer, each of the galvanized, cold-rolled steel plates was measured for electromagnetic shield effect at 60 Hz, and the results are given in Table 5, below. Also, the mechanical properties, such as yield strength and elongation, of the steel plates, were measured by use of a universal testing machine and summarized in Table 5, below.

Determined through observation with the naked eye and testing for coat adhesion, the platability of the hot-dip galvanized steel plates was expressed as ○ for a good state, and as X for the presence of fatal plating defects, in Table 5.

TABLE 5

| Composition | Component (Wt %) | | | | | Magnetic Shield | Electric Shield | Yield Strength | Hot-dip |
| --- | --- | --- | --- | --- | --- | --- | --- | --- | --- |
| No. | C | N | Si | Al | Mn | (dB) | (dB) | (Kg/mm$^2$) | Platability. |
| 7 | <0.003 | <0.003 | 0.2 | Tr. | 0.2 | 27.9 | 40.5 | 23.5 | ○ |
| 8 | <0.003 | <0.003 | 0.2 | Tr. | 0.4 | 28.2 | 40.3 | 21.8 | ○ |
| 9 | <0.003 | <0.003 | 0.2 | Tr. | 0.6 | 28.3 | 40.4 | 19.5 | ○ |
| 10 | <0.003 | <0.003 | 0.2 | Tr. | 0.8 | 26.8 | 40.3 | 21.3 | ○ |
| C. 6 | <0.003 | <0.003 | 0.2 | Tr. | 1.0 | 25.6 | 40.2 | 23.5 | X |
| 11 | <0.003 | <0.003 | Tr. | Tr. | 0.2 | 28.1 | 40.5 | 18.1 | ○ |
| C. 7 | <0.003 | <0.003 | Tr. | Tr. | Tr | 28.4 | 41.5 | 14.5 | ○ |

It is apparent from the data of Table 5 that steel plates which contained Mn in the content range defined in the present invention with the sum of Mn, Al, Si and P amounting to 1.0% or less (Composition Nos. 7 to 11), all were excellent in yield strength and electromagnetic shield capacity, as well as showing good platability.

By contrast, Comparative Composition No. C. 6 with an Mn content more than 0.8% and with the sum of Mn, Si, Al and P content 1.0% or higher was observed to have serious plating defects. On the other hand, Comparative Composition No. C. 7, even though excellent in electromagnetic shield capacity and hot-dip galvanization property, had so low a yield strength as to be unsuitable for use as general construction panels.

So excellent in terms of electromagnetic shield capacity, strength and processability are the steel plates of the present invention, in which the interstitial elements C, N and S as well as additive elements Si, Al, Mn and P are contained at controlled amounts, as described hereinbefore, that they are suitable as electromagnetic field shielding panels for use in construction and electric appliances.

What is claimed is:

1. A steel plate having an electrolytic galvanized coating thereon with shield effect against time-varying electromagnetic field at low frequency having a yield strength of 18 kg/mm$^2$ or higher, and an elongation of 40% or higher, comprising C in an amount of 0.003% by weight or less, N in an amount of 0.003% by weight or less, S in an amount of 0.009% by weight or less, C, N and S in an amount of 0.015% by weight or less in total; Mn in an amount of 0.1 to 1.0% by weight; Si in an amount of 0.5% by weight or less; Al in an amount of 1.0% by weight or less; P in an amount of 0.06% by weight or less; and Fe for the remainder, and inevitably present elements; and wherein the electrolytic galvanized coating is overlaid by a layer of far infrared radiation emitting powder which has a radiation efficiency of 0.9 with a thickness of 15–60 $\mu$m.

2. The steel plate as set forth in claim 1, wherein the electromagnetic shield effect is 26 dB or higher when the steel plate is 1 mm thick.

3. The steel plate as set forth in claim 1, further comprising an organic resin coating on the electrolytic galvanized coating.

4. The steel plate as set forth in claim 1, wherein the far infrared radiation emitting powder has a specific surface area of 1 m$^2$/g and comprises Mg(OH)$_2$ in an amount of 17–99% by weight.

5. A hot-dip galvanized steel plate with high shield effect against time-varying electromagnetic field at low frequency and yield strength, having a corrosion-resistant element coated thereon comprising C in an amount of 0.003% by weight or less, N in an amount of 0.003% by weight or less, S in an amount of 0.009% by weight or less, C, N and S in an amount of 0.015% by weight or less in total; Mn in an amount of 0.2 to 0.8% by weight; Al in an amount of 0.6% by weight or less; Si in an amount of 0.4% by weight or less; P in an amount of 0.06% by weight or less, with the proviso that the sum of Mn, Al, Si and P amounts to 0.2–1.0% by weight; and Fe for the remainder, and inevitably present elements.

6. The hot-dip galvanized steel plate as set forth in claim 5, wherein Al and Si are contained in amounts of 0.4% or less and 0.2% or less, respectively.

7. The hot-dip galvanized steel plate as set forth in claim 5, wherein the electromagnetic shield effect is 26 dB or higher when the steel plate is 1 mm thick and the yield strength is 18 kg/mm$^2$ or higher.

8. The hot-dip galvanized steel plate as set forth in claim 5, further comprising an organic resin coating on the hot-dip galvanized coating.

9. The hot-dip galvanized steel plate as set forth in claim 5, further comprising a layer of far infrared radiation emitting powder which has a far infrared emissivity of 0.9 or higher, at a thickness of 15–60 $\mu$m.

10. The hot-dip steel plate as set forth in claim 5, wherein the far infrared radiation emitting powder has a specific surface area of 1 m$^2$/g and comprises Mg(OH)$_2$ in an amount of 17–99% by weight.

* * * * *